(12) United States Patent
Heimel et al.

(10) Patent No.: US 7,945,395 B2
(45) Date of Patent: May 17, 2011

(54) METHOD FOR DETERMINING THE DENSITY OF FLUID MEDIA

(75) Inventors: Helmut Heimel, Graz (AT); Ulrike Rakusch, Graz (AT); Klaus Ritzmann, Graz (AT); Hans Stabinger, Graz (AT)

(73) Assignee: LABOR FUER MESSTECHNIK Dr. Hans Stabinger GmbH, Graz (AT)

( * ) Notice: Subject to any disclaimer, the term of this patent is extended or adjusted under 35 U.S.C. 154(b) by 61 days.

(21) Appl. No.: 12/270,363

(22) Filed: Nov. 13, 2008

(65) Prior Publication Data
US 2009/0126506 A1      May 21, 2009

(30) Foreign Application Priority Data

Nov. 16, 2007   (AT) ................ A 1865/2007

(51) Int. Cl.
*G01N 9/36*   (2006.01)
(52) U.S. Cl. ....... 702/25; 73/54.25; 73/861.08; 702/137
(58) Field of Classification Search ............... 702/22–25, 702/50, 54–56, 100, 137; 73/1.02, 1.73–1.74, 73/1.82–1.83, 19.03, 54.01–54.02, 54.41
See application file for complete search history.

(56) References Cited

U.S. PATENT DOCUMENTS

| | | | | | |
|---|---|---|---|---|---|
| 4,166,381 | A | * | 9/1979 | Woo | 73/54.25 |
| 4,508,127 | A | * | 4/1985 | Thurston | 137/8 |
| 6,651,511 | B1 | * | 11/2003 | Young | 73/861.08 |
| 6,668,621 | B1 | * | 12/2003 | Wright | 73/54.25 |

* cited by examiner

*Primary Examiner* — John H Le
(74) *Attorney, Agent, or Firm* — Kilpatrick Townsend & Stockton LLP

(57) ABSTRACT

The actual density of liquids is determined with a flexural oscillator that is excited at two different natural vibrations. The presence of air/gas inclusions or other inhomogeneities in a liquid is detected and their influence can be eliminated. In an initial step, the periods of the inherent vibrations and of at least one vibration damping value of the natural vibrations are determined for liquids having different densities ρ and viscosities. Liquid densities as well as the difference between them and between the vibration damping values are determined from this. An inclusion-free curve (KB) which reflects the functional dependence F(ρδ) between the relative density differences and the vibration damping differences is calculated and the exact function determined; i.e. the gas/air inclusion-free curve (KB) is expanded by introducing a deviation bandwidth (ab) to form an inclusion-free curve area (KF), which is stored. The functional value F(ρδ) of the liquid to be tested is determined and a check is performed to ascertain whether it is within the inclusion-free curve area and whether the resulting value of the density ρ is or is not applicable to the liquid being tested.

5 Claims, 1 Drawing Sheet

METHOD FOR DETERMINING THE DENSITY OF FLUID MEDIA

CROSS-REFERENCES TO RELATED APPLICATIONS

This application claims the priority of Austrian Patent Application No. A 1865/2007 filed Nov. 16, 2007, the disclosure of which is incorporated by reference.

BACKGROUND OF THE INVENTION

The present invention relates to a method for determining the actual density of liquids based on the period of a flexural oscillator filled with a fluid, e.g. liquid sample.

It is known to use flexural oscillators for determining the density of liquids and gases on the basis of electronically measuring the period of vibration of the flexural oscillator filled with the liquid from which the density of the liquid sample can be calculated.

To this end, the sample is placed in a hollow, U-shaped tube that forms the flexural oscillator, which is electronically excited to subject it to undamped vibration. The natural frequency of the flexural oscillator depends on the mass of the sample.

The two legs of the U-shaped oscillator tube form spring elements of the flexural oscillator. The direction of vibration is normal to a plane between the two legs.

The natural frequency of the flexural oscillator is affected by only that part of the liquid sample which actually participates in the vibration. The liquid volume that participates in the vibration is limited, for example, by stationary vibration nodes located at clamping points for the flexural oscillator of a natural frequency excitation device. If the oscillator is filled with the liquid sample at least up to the clamping points, the same, precisely defined volume always participates in the vibration, is constant for a given flexural oscillator, and the mass of the sample can be assumed to be directly proportional to its density and vice versa.

Overfilling of the flexural oscillator beyond the clamping points and/or excitation nodes points is irrelevant for the measurement. For this reason, the densities of liquid media flowing through a flexural oscillator can also be continuously measured. The technique of instantaneous direct density measurement of liquid media flowing through a flexural oscillator is used routinely in the beverage, petroleum and chemical industries, for example, and has the essential advantage that density measurements can be performed continuously on flowing liquid media in a fully automated manner.

In addition to temperature, the viscosity of the sample and, unfortunately, also inhomogeneities, e.g. agglomerates, air and/or gas inclusions or the like, if present, can affect the density measurement and falsify the results.

AT 400767B and EP 0568521 A1 address error corrections for such measurements based on the viscosity of the samples. In the disclosed embodiment, a fundamental vibration and a harmonic of same are excited at two different points of a flexural oscillator with an amplifying exciter. The influence of the viscosity of the sample on the measured density value is compensated for as described in detail in the references.

These methods of viscosity correction are also used in the devices currently being made available by applicants, in which excitation of the fundamental vibration and the harmonic in glass flexural oscillators differ somewhat as compared to the method disclosed in AT 400767B. However, this modified type of excitation represents the prevailing state of the art because it is part of the flexural oscillator devices currently used for measuring the density of liquid samples.

BRIEF SUMMARY OF THE INVENTION

The present invention is concerned with how inhomogeneities in samples, in particular air inclusions or bubbles in a liquid, affect density measurements and the elimination of such inhomogeneities on actual, measured density values. In particular the present invention serves to reliably and rapidly detect incorrectly measured density values that are caused by inhomogeneities in the liquid sample.

As already stated, especially air and other gas inclusions in a liquid sample often lead to incorrect measurements. The filling level of the flexural oscillator must therefore be monitored visually on an ongoing basis, e.g. through an inspection window, which results in increased work, effort and expense.

It is therefore an object of the present invention to improve the precision of density measurement and in particular the accuracy of the measurement results. An important advantage of the present invention is its automatic, nonoptical detection of sample inhomogeneities, such as gas and/or air inclusions entrained in a liquid, as well as its ability to automatically detect faulty measurements.

The invention is based on and improves the existing state of the art in the field of density determination with flexural oscillators and the error corrections that must be performed. This includes the flexural oscillator itself as well as exciting the liquid-filled oscillator with its two different natural oscillations, in particular with its one fundamental or base vibration and at least one harmonic in essentially any desired manner. It further includes the determination of the measurement results, namely the period of the two vibrations, e.g. the fundamental or base and the harmonic vibrations, as well as the associated vibration damping values for determining the density of the liquid sample, wherein temperature compensation viscosity compensations belong to the known state of the art.

In performing the novel method, the relative difference between a first vibration, namely the "low-frequency" vibration, e.g. the basic natural vibration of the liquid-filled flexural oscillator, and a second higher-frequency natural vibration, namely a harmonic of same and/or the difference in the damping at the two vibrations, is used to detect valid measured values. This may be done with or without viscosity compensation.

The present invention therefore provides a novel method for determining the actual density of fluid media according to claim 1.

The density difference and/or the relative density difference alone or the vibration damping difference divided by the square root of the density $\sqrt{\rho}$ (rho) can be sufficient to detect accurate, i.e. "valid", or correct, and "invalid", or incorrect, density values. This functions especially well on the basis of the functional dependence of the two measured variables on each another as illustrated in FIG. 3.

The exact analytical connection and/or parameters for the calculation need not be explained here in great detail. The novel method of the present invention relates in general to the detection and/or determination of "valid" measured values and especially "invalid" measured values, the correctness of which is determined by inhomogeneities such as air (or gas) inclusions in the liquid. The measured values determined with the flexural oscillator indicate percentage ranges, for example, over which a measured value determined and analyzed by means of the present invention remains acceptable.

With regard to the state of the art in the field of detection of air (gas) inclusions in liquid samples, it should be noted that one way of detecting them is a measurement error caused by the inclusions based on finding a physical measured value which is known from U.S. Pat. No. 7,231,805 B2, for example. According to its disclosure, the pressure is measured near the nozzle of a dispenser, and suitable circuitry recognizes deviations in the pressure measurements as being caused by the inclusions and/or by disturbances.

In addition, an automatic, optical density meter capable of detecting false measured density values for the liquid due to inclusions in the liquid is publicly known from a technical exhibition. This device detects inclusions in a liquid sample with a camera instead of the usual inspection window with which the filling level of a flexural oscillator can be checked.

As set forth in claim 2, the fundamental vibration is advantageously used as the natural vibration with a lower frequency (G) and the first harmonic of the flexural oscillator is used as the natural vibration with the higher frequency (O).

Claim 3 broadly addresses, FIGS. 1 and 2 illustrate, and the following further explains how the mathematical functions that form the basis for the illustrations are used.

Errors in measurements with flexural oscillator density meters are to a large extent due to gas inclusions that are introduced into the density measurement cell, i.e. the flexural oscillator, during filling or are formed by the liquid sample due to outgassing in the measurement cell.

As briefly mentioned above, whether the measurement cell has been filled without inclusions can be visually monitored. Very small inclusions or inclusions in an opaque sample cannot be discovered in this manner. In such case, repeat measurements and discarding obvious extremes are somewhat helpful but not very reliable and/or accurate.

The method of the present invention makes it possible to detect faulty density measurements caused by gas/air inclusions and/or other inhomogeneities in fluids, and in particular in liquids, by analyzing density damping values and vibration damping values measured for two different vibration modes of the flexural oscillator in a process that can be automated to help prevent future occurrences of faulty density measurements.

DETAILED DESCRIPTION OF THE INVENTION

With regard to the principle of the density measurement method of the present invention, the following applies:

The flexural oscillators can be operated in a variety of vibration modes. For example, the two vibration modes diagrammed in FIGS. 1a and 1b are already being used with density meters for density measurements and for correcting viscosity errors as follows.

Figure 1A:
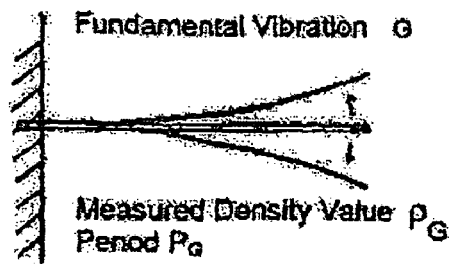
FIGS. 1a and 1b illustrate base and harmonic vibrators encountered in flexural oscillators.
Figure 1B:
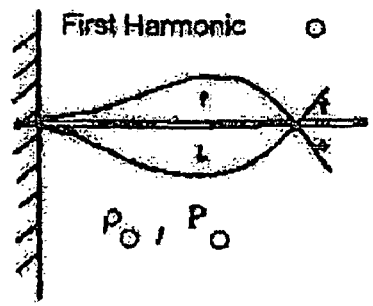

FIGS. 1a and 1b, for example, show the first two vibration modes of a flexural oscillator which is clamped or fixed at one end and has a fundamental vibration G and a first harmonic O.

A measured density value $\rho_G$ and the vibration period $P_G$ are determined from the data for the first natural vibration and/or the lower-frequency natural vibration, and in particular the natural fundamental vibration of the flexural oscillator filled with liquid. The measured density value $\rho_O$, the harmonic period $P_O$ and the harmonic damping $\delta_O$ are determined from the data for the second natural vibration and/or the higher-frequency natural vibration, i.e. the first harmonic in particular.

The density values $\rho_G$ and $\rho_O$ not corrected for viscosity in these two vibration modes are calculated from the period, i.e. vibration period values $P_G$ and $P_O$ measured in the respective mode in accordance with $$\rho_G = A_G \cdot P_G^2 - B_G \text{ and } \rho_O = A_O \cdot P_O^2 - B_O.$$

The constants $A_G$, $B_G$ and/or $A_O$, $B_O$ are characteristic of the respective flexural oscillator and are determined with measurements of samples having a low viscosity $\eta$ and a known density $\rho$.

During adjustments as well as measurements, the flexural oscillator must be filled homogeneously, i.e. without inclusions. When measuring liquid samples of a relatively higher viscosity $\eta$ and a known density $\rho$, a measurement error is noted that increases with the viscosity of the sample. This measurement error is greater for the first harmonic mode O than for the fundamental vibration and reaches a greater maximum value with higher viscosities.

If the vibration damping $\delta$ is also measured, it has a larger value for the first harmonic than the fundamental vibration G. This value becomes a much higher maximum value at higher viscosities than for the fundamental vibration G and then also drops again. The values for vibration damping $\delta$ can be determined by causing the height of the amplitudes of the natural vibration to fluctuate.

Figure 2A:
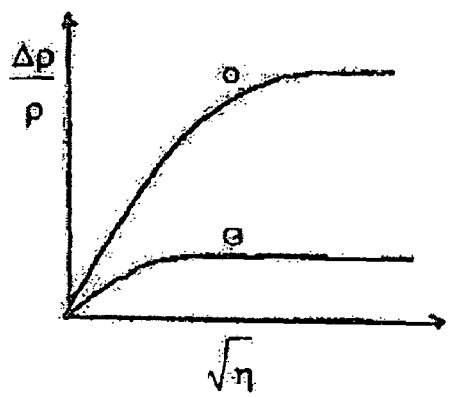
FIGS. 2a and 2b illustrate relative density errors $\Delta\rho/\rho$ and damping differences $\Delta\delta$.
Figure 2B:
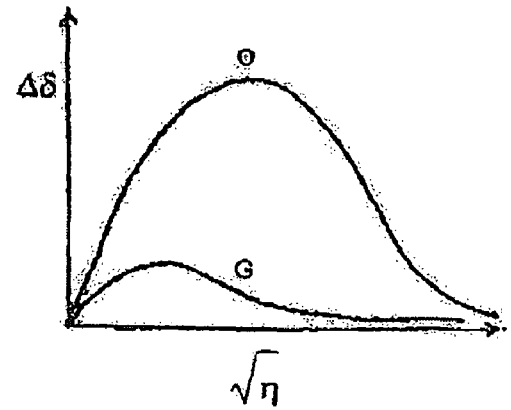

FIGS. 2a and 2b illustrate this in more detail. They show the relative density error $\Delta\rho/\rho$ and the damping difference $\Delta\delta$ caused by the sample viscosity for the fundamental vibration and the first harmonic of the flexural oscillator filled with a homogenous sample, i.e. a liquid sample without air (or gas) inclusions, as a function of the square root of the viscosity of the sample.

In addition, the damping difference $\Delta\delta = \delta - \delta_{air}$ caused by the viscosity of the sample is used.

From the relationships schematically shown in FIGS. 2a and 2b, the viscosity-induced error with regard to density and damping can be calculated and compensated for.

The just-described measured values needed for the viscosity correction are used to detect faulty measurements caused by air/gas inclusions or other inhomogeneities in the liquid that is to be tested.

Figure 3A:
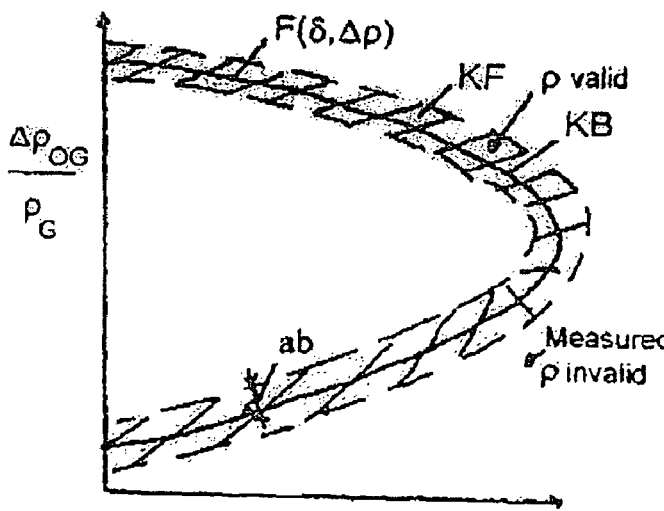
FIGS. 3a and 3b illustrate the functional dependence of the density difference and the vibration damping difference divided by the square root of the density.

Homogeneous samples have a well-defined relationship with an approximately parabolic curve between the relative density difference $\Delta\rho = (\rho_O - \rho_G)/\rho_G$ and the damping difference $\Delta\delta_O$ divided by $\sqrt{\rho}$. As can be seen in FIG. 3a, this relationship has an approximately parabolic shape that defines the inclusion-free curve KB.

FIG. 3a shows the relationship between the relative density difference $\Delta_{\rho O} = (\rho_O - \rho_G)/\rho_G$ and the damping difference $\Delta\delta_O$ of the first harmonic O divided by the square root of the density value $\rho_G$ of the fundamental vibration G for homogeneous samples and the possible valid and invalid measurements, based on the inclusion-free curve area KF, which has been expanded by the distance "ab" on both sides of the inclusion-free curve KB.

The exact inclusion-free curve KB spreads out from both sides based on values for $(\rho_O - \rho_G)/\rho_G$ and $\Delta\delta_O \sqrt{\rho_G}$ determined for a specific liquid sample. For liquids without gas inclusions, these values are within the cross-hatched area in FIG. 3a.

When the liquid in the flexural oscillator has gas inclusions, the density values ρ measured for the two vibration modes G, O defined above are influenced in different ways. The vibration damping $\Delta\delta_O$ measured for the first harmonic O usually increases greatly. As a result, there can be points outside of the relationship reflected by the "parabolic area" KF, which applies to homogeneous, i.e. inclusion-free, liquid samples in the diagram in FIG. 3a.

Thus, to make use of the relationship that applies to inclusion-free samples, a range can be defined that takes account of the reproducibility of measurements of homogeneous samples and the measurement uncertainties within which density measurements are to be considered as valid or acceptable and outside of which such measurements are to be considered invalid or unacceptable.

For example, a value of "±5% bandwidth" based on the lower value of Δρ when $\Delta\delta_O=0$ might be provided on both sides of the exact, inclusion-free curve KB.

Instead of density values $\rho_G$ and $\rho_O$ that have not been corrected for viscosity, with a suitable viscosity correction, the density values corrected for both vibration modes G, O that are used can also be employed.

In the event of trouble-free filling of the measurement cell, these density values will largely match. With faulty filling, the two viscosity-corrected density values become falsified in different ways. In such a case, the damping difference $\Delta\delta_O$ will be greater than it would be with a correct filling.

Figure 3B:
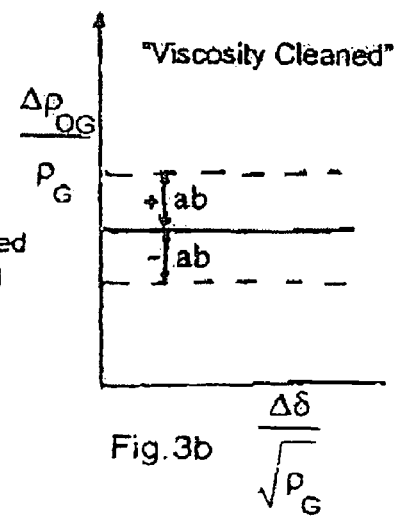

Instead of the relationship illustrated in FIG. 3a, a linear relationship then occurs as is shown in FIG. 3b.

FIG. 3b shows the relative difference in the viscosity-corrected densities ρ measured for the fundamental vibration G and the first harmonic O as a function of the damping difference.

Instead of the parabola-like inclusion-free curve KB' shown in FIG. 3a, a constant linear curve KB is obtained in this "viscosity-corrected" diagram, again accompanied on both sides by a "tolerance band" of, for example, ±5% of the value of the points on the curve, so that an inclusion-free curve area KF becomes again available for evaluating the presence or absence of inclusions.

For a liquid to be tested, the respective period and vibration damping values for the fundamental vibration G and the first harmonic O, for example, are measured and the actual value $F_{GO}$ for the measured values is determined on the basis of the functional relationship F(ρδ). When the value of the function $F_{GO}$ determined for a liquid to be tested is within the curve area KF, the value of the density ρ determined for the liquid to be tested for its density is acceptable. When the value for the function $F_{GO}$ is outside the curve area KF, then the density value has been falsified by air inclusions and/or inhomogeneities in the sample.

Simultaneously with the inventive analysis of the density data of a liquid to be tested with the flexural oscillator, it is advantageous to additionally optically analyze the liquid in a flexural oscillator that is filled with it with a video recorder, a camera or a CCD device. When inclusions and/or inhomogeneities are detected based on the described density analysis, the results of the optical analysis can be stored and archived. When desired, incorrect measurements caused by inclusions can then be further evaluated with the results of the optical analysis of the liquid sample.

The density determination method of the present invention to eliminate density values falsified due to inclusions in the samples does not work as well when small inclusions are uniformly distributed in a highly viscous sample because in such in event the sample appears as a homogeneous substance for both selected vibration modes. Due to the high viscosity of such samples, the damping, which would otherwise greatly increase due to relative movement of the inclusions in the sample, is hardly affected at all.

In such cases, however, even the optical method will yield poor results because of the small size of the inclusions.

What is claimed is:

1. Method for determining the density of a liquid by density meters with a flexural oscillator holding the liquid to be measured therein on the basis of measuring periods of oscillation at two different natural vibrations of the flexural oscillator and of at least a vibration damping value at one of the natural vibrations to find out whether air inclusions and/or other inhomogeneities are present in the liquid or not to decide if the measured density value is correct or not, the method comprising:

(a) determining the periods of oscillation of the flexural oscillator when filled with inclusion-free samples of different densities ρ and viscosities η at two different natural vibrations and of at least one characteristic vibration damping value δ at one of the natural vibrations, (b) calculating from the measured period values at the natural vibration having the lower frequency the density values $\rho_G$ for each of the samples and from the measured period values at the natural vibration having the higher frequency density values $\rho_O$, (c) calculating a functional dependence $(\delta, \Delta\rho_{OG})$ between the relative density differences $$\Delta\rho_{OG}\left(=\frac{\rho_O - \rho_G}{\rho_O}\right) \text{ or } \Delta\rho_{OG}\left(=\frac{\rho_O - \rho_G}{\rho_G}\right)$$

in which the density values $\rho_O$ and $\rho_G$ are respectively viscosity-corrected or not viscosity-corrected, and the measured vibration damping values δ of the samples to define an inclusion-free curve KB reflecting the functional dependency $(\delta, \Delta\rho_{OG})$ over a desired density and viscosity range, (d) expanding the inclusion-free curve KB to provide an inclusion-free curve area KF having a deviation bandwidth on both sides of the curve KB and a constant distance in a direction normal to the curve KB, (e) storing the inclusion-free curve area KF, (f) for each subsequent liquid sample the density of which is to be measured with the flexural oscillator, determining the actual functional value $(\delta, \Delta\rho_{OG})$ from the actual values of $\rho_G, \rho_O$ and δ, and (g) testing whether the actual functional value $F(\delta, \Delta\rho_{OG})$ falls within the boundaries of the inclusion-free curve area KF or not and therewith deciding whether the measured density value of the liquid sample is correct.

2. A method according to claim 1, wherein the characteristic damping value Δδ is determined by the respective vibration damping values $\delta_O$ when the flexural oscillator is filled with the liquid at the second natural vibration or $\delta_G$ when the flexural oscillator is filled with the liquid at the first natural vibration and normalized to $\Delta\delta/\sqrt{\rho}$ by subtracting the measured damping value $\delta_{OL}$ when the flexural oscillator is not filled with the liquid at the second natural vibration or $\delta_{GL}$ when the flexural oscillator is filled with the liquid at the first natural vibration and dividing by the square root of $\rho_O$ or $\rho_G$, for example:

$$\frac{\Delta \delta_O}{\sqrt{\rho_O}} \left( = \frac{\delta_O - \delta_{OL}}{\sqrt{\rho_O}} \right) \text{ or } \frac{\Delta \delta_O}{\sqrt{\rho_G}} \left( = \frac{\delta_O - \delta_{OL}}{\sqrt{\rho_G}} \right)$$

and/or $$\frac{\Delta \delta_O}{\sqrt{\rho_G}} \left( = \frac{\delta_G - \delta_{GL}}{\sqrt{\rho_G}} \right)$$

wherein $\delta_O$ is the determined damping value of the natural vibration having the higher frequency, $\delta_G$ is the determined damping value of the natural vibration having the lower frequency, $\delta_{OL}$ is the determined damping value of the empty flexural oscillator at the natural vibration having the higher frequency, $\delta_{GL}$ is the determined damping value of the empty flexural oscillator at the natural vibration having the lower frequency, $\delta_O$ is the difference $\delta_O$ minus $\delta_{OL}$ at the natural vibration having the lower frequency, and $\delta_G$ is the difference $\delta_G$-$\delta_{GL}$ at the natural vibration having the lower frequency.

3. A method of claim 1, wherein the calculated values of the liquid density are viscosity-corrected.

4. A method of claim 1, wherein the first natural vibration which has a lower frequency (G) excited by the amplifying exciter, is the fundamental vibration of the flexural oscillator, and the second natural vibration, which has a higher frequency (O), is the first harmonic of the flexural oscillator.

5. A method according to claim 1, including comparing an optical analysis with a video, camera or CCD photosensor arrangement of the flexural oscillator when filled with the liquid to be tested with result of the density analysis with regard to the inclusions that are present or not present in the liquid, and when the fact that the liquid is free of inclusions and/or inhomogeneities is confirmed the density value is thereby ascertained identified as correct by optical analysis with accurate and/or positive results of the density test.

* * * * *